United States Patent
Bales, Jr. et al.

(10) Patent No.: US 10,342,685 B2
(45) Date of Patent: Jul. 9, 2019

(54) STENT AND METHOD FOR MANUFACTURING THE STENT

(71) Applicant: Angiomed GmbH & Co. Medizintechnik KG, Karlsruhe (DE)

(72) Inventors: Thomas O. Bales, Jr., Miami, FL (US); Charles R. Slater, Fort Lauderdale, FL (US); Scott Jahrmarkt, Miami, FL (US)

(73) Assignee: Angiomed GmbH & Co. Medizintechnik KG, Karlsruhe (DE)

(*) Notice: Subject to any disclaimer, the term of this patent is extended or adjusted under 35 U.S.C. 154(b) by 100 days.

(21) Appl. No.: 15/282,735

(22) Filed: Sep. 30, 2016

(65) Prior Publication Data

US 2017/0020698 A1    Jan. 26, 2017

Related U.S. Application Data

(63) Continuation of application No. 13/871,942, filed on Apr. 26, 2013, now Pat. No. 9,486,339, which is a
(Continued)

(51) Int. Cl.
*A61F 2/88* (2006.01)
*A61F 2/91* (2013.01)
(Continued)

(52) U.S. Cl.
CPC ............... *A61F 2/88* (2013.01); *A61F 2/844* (2013.01); *A61F 2/91* (2013.01); *A61F 2/915* (2013.01);
(Continued)

(58) Field of Classification Search
CPC .... A61F 2/88; A61F 2/915; A61F 2/91; A61F 2250/0098; A61F 2/07; A61F 2/82; A61F 2230/0091
See application file for complete search history.

(56) References Cited

U.S. PATENT DOCUMENTS

| | | |
|---|---|---|
| 4,886,062 A | 12/1989 | Wiktor |
| 5,091,205 A | 2/1992 | Fan |

(Continued)

FOREIGN PATENT DOCUMENTS

| | | |
|---|---|---|
| CA | 2155527 A1 | 8/1994 |
| DE | 2544371 A1 | 7/1985 |

(Continued)

OTHER PUBLICATIONS

EP 07717595.8 European Search Report dated Nov. 4, 2013.
(Continued)

*Primary Examiner* — Anh T Dang
(74) *Attorney, Agent, or Firm* — Rutan & Tucker, LLP

(57) ABSTRACT

A stent includes a series of helical windings defining an outer circumference of a cylinder. The helical windings include a plurality of struts having straight portions connected by curved portions. The straight portions may be substantially aligned with a longitudinal axis of the stent when the stent is in a reduced state. A plurality of bridges connect adjacent windings. The bridges may be substantially orthogonal to the longitudinal axis of the stent in the reduced state. A plurality of radiopaque members extend from a terminal helical winding. The radiopaque members include an extension portion and an end portion. The extension portion may have a first width and the end portion may have a second width greater than the first width. The end portion may include an extreme end substantially orthogonal to the longitudinal axis of the stent.

16 Claims, 10 Drawing Sheets

Related U.S. Application Data continuation of application No. 11/216,293, filed on Aug. 31, 2005, now abandoned.

(60) Provisional application No. 60/606,261, filed on Sep. 1, 2004.

(51) Int. Cl.

| | | |
|---|---|---|
| *A61F 2/915* | | (2013.01) |
| *A61F 2/844* | | (2013.01) |
| *A61F 2/848* | | (2013.01) |
| *A61F 2/08* | | (2006.01) |
| *A61F 2/966* | | (2013.01) |

(52) U.S. Cl.
CPC ....... *A61F 2/848* (2013.01); *A61F 2002/0864* (2013.01); *A61F 2002/91533* (2013.01); *A61F 2002/91541* (2013.01); *A61F 2002/91558* (2013.01); *A61F 2002/91583* (2013.01); *A61F 2002/9665* (2013.01); *A61F 2250/0098* (2013.01)

(56) References Cited

U.S. PATENT DOCUMENTS

| | | | |
|---|---|---|---|
| 5,292,331 A | 3/1994 | Boneau | |
| 5,314,472 A | 5/1994 | Fontaine | |
| 5,356,423 A | 10/1994 | Tihon et al. | |
| 5,370,683 A | 12/1994 | Fontaine | |
| 5,421,955 A | 6/1995 | Lau | |
| 5,514,154 A | 5/1996 | Lau et al. | |
| 5,540,712 A | 7/1996 | Kleshinski et al. | |
| 5,562,697 A | 10/1996 | Christiansen | |
| 5,569,295 A | 10/1996 | Lam | |
| 5,591,197 A | 1/1997 | Orth et al. | |
| 5,630,829 A | 5/1997 | Lauterjung | |
| 5,649,952 A | 7/1997 | Lam | |
| 5,653,727 A | 8/1997 | Wiktor | |
| 5,665,115 A | 9/1997 | Cragg | |
| 5,716,393 A | 2/1998 | Lindenberg et al. | |
| 5,716,396 A | 2/1998 | Williams, Jr. | |
| 5,725,572 A | 3/1998 | Lam et al. | |
| 5,741,327 A | 4/1998 | Frantzen | |
| 5,776,161 A | 7/1998 | Globerman | |
| 5,780,807 A | 7/1998 | Saunders | |
| 5,800,456 A | 9/1998 | Maeda et al. | |
| 5,800,520 A | 9/1998 | Fogarty et al. | |
| 5,810,870 A | 9/1998 | Myers et al. | |
| 5,810,872 A | 9/1998 | Kanesaka et al. | |
| 5,824,043 A | 10/1998 | Cottone, Jr. | |
| 5,824,059 A | 10/1998 | Wijay | |
| 5,843,175 A | 12/1998 | Frantzen | |
| 5,861,027 A | 1/1999 | Trapp | |
| 5,868,781 A | 2/1999 | Killion | |
| 5,891,191 A | 4/1999 | Stinson | |
| 5,895,406 A | 4/1999 | Gray | |
| 5,902,317 A | 5/1999 | Kleshinski et al. | |
| 5,906,639 A | 5/1999 | Rudnick et al. | |
| 5,911,754 A | 6/1999 | Kanesaka et al. | |
| 5,913,897 A | 6/1999 | Corso, Jr. et al. | |
| 5,922,021 A | 7/1999 | Jang | |
| 5,925,061 A | 7/1999 | Ogi et al. | |
| 5,935,162 A | 8/1999 | Dang | |
| 5,968,088 A | 10/1999 | Hansen et al. | |
| 5,985,061 A | 11/1999 | Doi et al. | |
| 6,013,854 A | 1/2000 | Moriuchi | |
| 6,019,789 A | 2/2000 | Dinh et al. | |
| 6,022,374 A | 2/2000 | Imran | |
| 6,042,597 A | 3/2000 | Kveen et al. | |
| 6,042,605 A | 3/2000 | Martin et al. | |
| 6,053,940 A | 4/2000 | Wijay | |
| 6,059,808 A | 5/2000 | Boussignac et al. | |
| 6,059,822 A | 5/2000 | Kanesaka et al. | |
| 6,063,113 A | 5/2000 | Kavteladze et al. | |
| 6,066,167 A | 5/2000 | Lau et al. | |
| 6,117,165 A | 9/2000 | Becker | |
| 6,129,755 A | 10/2000 | Mathis et al. | |
| 6,152,957 A | 11/2000 | Jang | |
| 6,190,406 B1 | 2/2001 | Duerig et al. | |
| 6,203,568 B1 | 3/2001 | Lombardi et al. | |
| 6,238,409 B1 | 5/2001 | Hojeibane | |
| 6,238,430 B1 | 5/2001 | Klumb et al. | |
| 6,245,100 B1 | 6/2001 | Davila et al. | |
| 6,248,122 B1 | 6/2001 | Klumb et al. | |
| 6,251,135 B1 | 6/2001 | Stinson et al. | |
| 6,273,911 B1 | 8/2001 | Cox et al. | |
| 6,293,966 B1 | 9/2001 | Frantzen | |
| 6,315,794 B1 | 11/2001 | Richter | |
| 6,325,820 B1 | 12/2001 | Khosravi et al. | |
| 6,342,067 B1 | 1/2002 | Mathis et al. | |
| 6,348,065 B1 | 2/2002 | Brown et al. | |
| 6,352,552 B1 | 3/2002 | Levinson et al. | |
| 6,361,557 B1 | 3/2002 | Gittings et al. | |
| 6,423,091 B1 | 7/2002 | Hojeibane | |
| 6,475,236 B1 | 11/2002 | Roubin et al. | |
| 6,485,509 B2 | 11/2002 | Killion et al. | |
| 6,485,511 B2 | 11/2002 | Lau et al. | |
| 6,488,700 B2 | 12/2002 | Klumb et al. | |
| 6,488,701 B1 | 12/2002 | Nolting et al. | |
| 6,488,703 B1 | 12/2002 | Kveen et al. | |
| 6,503,271 B2 | 1/2003 | Duerig et al. | |
| 6,517,570 B1 | 2/2003 | Lau et al. | |
| 6,520,987 B1 | 2/2003 | Plante | |
| 6,527,938 B2 | 3/2003 | Bales et al. | |
| 6,533,807 B2 | 3/2003 | Wolinsky et al. | |
| 6,537,310 B1 | 3/2003 | Palmaz et al. | |
| 6,551,351 B2 | 4/2003 | Smith et al. | |
| 6,572,647 B1 | 6/2003 | Supper et al. | |
| 6,585,755 B2 | 7/2003 | Jackson et al. | |
| 6,613,081 B2 | 9/2003 | Kim et al. | |
| 6,645,237 B2 | 11/2003 | Klumb et al. | |
| 6,656,219 B1 | 12/2003 | Wiktor | |
| 6,660,019 B1 | 12/2003 | Richter et al. | |
| 6,660,032 B2 | 12/2003 | Klumb et al. | |
| 6,692,522 B1 * | 2/2004 | Richter | A61F 2/91 623/1.15 |
| 6,702,807 B2 | 3/2004 | Peyman | |
| 6,719,782 B1 | 4/2004 | Chuter | |
| 6,730,116 B1 | 5/2004 | Wolinsky et al. | |
| 6,733,524 B2 | 5/2004 | Tseng et al. | |
| 6,740,114 B2 | 5/2004 | Burgermeister | |
| 6,755,856 B2 | 6/2004 | Fierens et al. | |
| 6,776,793 B2 | 8/2004 | Brown et al. | |
| 6,776,794 B1 | 8/2004 | Hong et al. | |
| 6,814,746 B2 | 11/2004 | Thompson et al. | |
| 6,852,124 B2 | 2/2005 | Cox et al. | |
| 6,862,794 B2 | 3/2005 | Hopkins | |
| 6,863,685 B2 | 3/2005 | Davila et al. | |
| 6,866,669 B2 | 3/2005 | Buzzard et al. | |
| 6,878,162 B2 | 4/2005 | Bales et al. | |
| 6,918,928 B2 | 7/2005 | Wolinsky et al. | |
| 6,923,828 B1 | 8/2005 | Wiktor | |
| 6,935,404 B2 | 8/2005 | Duerig et al. | |
| 6,939,352 B2 | 9/2005 | Buzzard et al. | |
| 6,949,120 B2 | 9/2005 | Kveen et al. | |
| 6,969,402 B2 | 11/2005 | Bales et al. | |
| 6,976,994 B2 | 12/2005 | Ballou et al. | |
| 7,004,968 B2 | 2/2006 | Lootz et al. | |
| 7,025,777 B2 | 4/2006 | Moore | |
| 7,033,385 B2 | 4/2006 | Eder et al. | |
| 7,034,821 B2 | 4/2006 | Baumberg | |
| 7,037,330 B1 | 5/2006 | Rivelli, Jr. et al. | |
| 7,037,331 B2 | 5/2006 | Mitelberg et al. | |
| 7,128,752 B2 | 10/2006 | Bales | |
| 7,131,993 B2 | 11/2006 | Gregorich | |
| 7,169,175 B2 | 1/2007 | Cottone, Jr. et al. | |
| 7,172,623 B2 | 2/2007 | Hansen et al. | |
| 7,195,648 B2 | 3/2007 | Jones et al. | |
| 7,214,229 B2 | 5/2007 | Mitchell et al. | |
| 7,243,408 B2 | 7/2007 | Vietmeier | |
| 7,273,494 B2 | 9/2007 | Rolando et al. | |
| 7,326,245 B2 | 2/2008 | Rosenthal et al. | |
| 7,331,986 B2 | 2/2008 | Brown et al. | |
| 7,758,624 B2 | 7/2010 | Dorn et al. | |

(56) References Cited

U.S. PATENT DOCUMENTS

| | | | |
|---|---|---|---|
| 7,763,067 B2 | 7/2010 | Bales et al. | |
| 7,771,411 B2 | 8/2010 | Smith et al. | |
| 7,780,721 B2 | 8/2010 | Bales et al. | |
| 7,972,355 B2 | 7/2011 | Bales | |
| 7,993,384 B2 | 8/2011 | Wu et al. | |
| 8,002,818 B2 | 8/2011 | Bregulla | |
| 8,038,707 B2 | 10/2011 | Bales et al. | |
| 8,328,865 B2 | 12/2012 | Bales, Jr. et al. | |
| 8,333,799 B2 | 12/2012 | Bales, Jr. et al. | |
| 8,512,391 B2 | 8/2013 | Bales, Jr. et al. | |
| 8,672,994 B2 | 3/2014 | Kaplan et al. | |
| 9,049,360 B2 | 6/2015 | Jo et al. | |
| 9,456,911 B2 | 10/2016 | Bales, Jr. et al. | |
| 9,486,339 B2 | 11/2016 | Bales, Jr. et al. | |
| 2002/0143386 A1* | 10/2002 | Davila | A61F 2/91 623/1.15 |
| 2003/0050690 A1* | 3/2003 | Kveen | A61F 2/91 623/1.15 |
| 2003/0055485 A1 | 3/2003 | Lee et al. | |
| 2003/0108659 A1 | 6/2003 | Bales et al. | |
| 2004/0015229 A1 | 1/2004 | Fulkerson et al. | |
| 2004/0054398 A1 | 3/2004 | Cully et al. | |
| 2004/0093066 A1 | 5/2004 | Durcan | |
| 2004/0153142 A1 | 8/2004 | Klumb et al. | |
| 2004/0172127 A1* | 9/2004 | Kantor | A61F 2/90 623/1.16 |
| 2005/0060025 A1* | 3/2005 | Mackiewicz | A61F 2/91 623/1.34 |
| 2005/0107738 A1 | 5/2005 | Slater et al. | |
| 2005/0113798 A1 | 5/2005 | Slater et al. | |
| 2006/0004437 A1 | 1/2006 | Jayaraman | |
| 2006/0060266 A1 | 3/2006 | Bales et al. | |
| 2006/0064155 A1 | 3/2006 | Bales et al. | |
| 2006/0074480 A1 | 4/2006 | Bales et al. | |
| 2013/0090719 A1 | 4/2013 | Bales, Jr. et al. | |
| 2013/0090721 A1 | 4/2013 | Bales, Jr. et al. | |

FOREIGN PATENT DOCUMENTS

| | | |
|---|---|---|
| DE | 29516712 U1 | 12/1995 |
| DE | 19539449 A1 | 4/1997 |
| DE | 29816878 U1 | 12/1998 |
| DE | 29522101 U1 | 12/1999 |
| DE | 19901530 A1 | 7/2000 |
| DE | 20019429 U1 | 3/2002 |
| DE | 69521346 T2 | 4/2002 |
| EP | 0688545 A1 | 12/1995 |
| EP | 0712614 A1 | 5/1996 |
| EP | 0732088 A2 | 9/1996 |
| EP | 0790041 A2 | 8/1997 |
| EP | 0792627 A2 | 9/1997 |
| EP | 0945107 A2 | 9/1999 |
| EP | 1132058 A1 | 9/2001 |
| EP | 1155664 A2 | 11/2001 |
| FR | 2760351 A1 | 9/1998 |
| WO | 9618359 A1 | 6/1996 |
| WO | 9628116 A1 | 9/1996 |
| WO | 9830173 A1 | 7/1998 |
| WO | 9838945 A1 | 9/1998 |
| WO | 0016718 A1 | 3/2000 |
| WO | 0024340 A1 | 5/2000 |
| WO | 0049973 A2 | 8/2000 |
| WO | 0050116 A1 | 8/2000 |
| WO | 0132102 A1 | 5/2001 |
| WO | 0189421 A2 | 11/2001 |
| WO | 2004019818 A2 | 3/2004 |
| WO | 2006005026 A2 | 1/2006 |
| WO | 2006026777 A2 | 3/2006 |
| WO | 2006026778 A2 | 3/2006 |
| WO | 2006026779 A2 | 3/2006 |
| WO | 2006026781 A2 | 3/2006 |
| WO | 2006026782 A2 | 3/2006 |
| WO | 2007003591 A1 | 1/2007 |
| WO | 2007095466 A2 | 8/2007 |
| WO | 2008100780 A2 | 8/2008 |
| WO | 2008100783 A2 | 8/2008 |

OTHER PUBLICATIONS

Designation: ASTM F67-06 Standard Specification for Unalloyed Titanium, for Surgical Implant Applications (UNS 1 R50250, UNS R50400, UNS R50550, UNS R50700) Active Standard ASTM F67 Developed by Subcommittee: F04.12, D Book of Standards vol. 13.01.

Designation: ASTM B348-05 Standard Specification for Titanium and Titanium Alloy Bars and Billets Active Standard ASTM B348 Developed by Subcommittee: B10.01, Book of Standards vol. 02.04.

EP 05796577.4 European Seach Report dated Feb. 12, 2013.

EP 05796752.3 European Search Report dated Mar. 26, 2013.

EP Application No. 05810201 filed Jan. 19, 2005 EP Search Report dated Aug. 7, 2008.

EP Application No. 10177855.3 filed Aug. 26, 2003 Examination Report dated Apr. 12, 2012.

Haas, Schuessler, Welding and Joining of TiNi Shape Memory Alloys: Engineering Aspects and Medical Applications. Proceedings First European Conference on Shape Memory and Superelastic Technolgoies SMST-99, Belguim (1999).

Kastrati, A. Clinical Impact of Stent Design 2: Results From Randomized Trials TCT2003.

PCT/DE1999/002980 filed Sep. 20, 1999 Search Report dated Feb. 3, 2000.

PCT/EP2003/009570 filed Aug. 26, 2003 Search Report dated Mar. 26, 2004.

PCT/US2005/031556 filed Sep. 1, 2005 International Preliminary Report on Patentability dated Feb. 24, 2009.

PCT/US2005/031556 filed Sep. 1, 2005 Search Report on Patentability dated Jan. 17, 2008.

PCT/US2005/031556 filed Sep. 1, 2005 Written Opinion dated Jan. 17, 2008.

PCT/US2005/031557 filed Sep. 1, 2005 International Preliminary Report on Patentability dated Oct. 16, 2007.

PCT/US2005/031557 filed Sep. 1, 2005 Search Report dated Sep. 25, 2007.

PCT/US2005/031557 filed Sep. 1, 2005 Written Opinion dated Sep. 13, 2007.

PCT/US2005/031571 filed Sep. 1, 2005 International Preliminary Report on Patentability dated Mar. 6, 2007.

PCT/US2005/031571 filed Sep. 1, 2005 Search Report dated Aug. 30, 2006.

PCT/US2005/031571 filed Sep. 1, 2005 Written Opinion dated Jul. 14, 2006.

PCT/US2005/031618 filed Sep. 1, 2005 International Preliminary Report on Patentability dated Nov. 6, 2007.

PCT/US2005/031618 filed Sep. 1, 2005 Search Report dated Sep. 20, 2007.

PCT/US2005/031618 filed Sep. 1, 2005 Written Opinion dated Jul. 9, 2007.

PCT/US2005/031619 filed Sep. 1, 2005 International Preliminary Report on Patentability dated Sep. 11, 2007.

PCT/US2005/031619 filed Sep. 1, 2005 Search Report dated Jul. 27, 2007.

PCT/US2005/031619 filed Sep. 1, 2005 Written Opinion dated Jul. 13, 2007.

PCT/US2007/061917 filed Dec. 9, 2007 International Preliminary Report on Patentability dated Aug. 19, 2008.

PCT/US2007/061917 filed Dec. 9, 2007 Search Report dated Mar. 17, 2008.

PCT/US2007/061917 filed Dec. 9, 2007 Written Opinion dated Mar. 17, 2008.

PCT/US2008/053319 filed Feb. 7, 2008 International Preliminary Report on Patentability dated Aug. 19, 2009.

PCT/US2008/053319 filed Feb. 7, 2008 Search Report dated Aug. 1, 2008.

(56) References Cited

OTHER PUBLICATIONS

PCT/US2008/053319 filed Feb. 7, 2008 Written Opinion dated Aug. 1, 2008.
Siekmeyer, Steegmuller, Schrader, Hegel, Strobel, Schuessler, Novel Micro-Joining Techniques to Improve Stent 35 Radiopacity, a Comparison of Welding and Riveting Processes, Proceedings of the Materials & Processes for Medical Devices Conference, Boston (2005).
PCT/US2008/053326 filed Feb. 7, 2008 Search Report dated Jul. 31, 2008.
PCT/US2008/053326 filed on Feb. 12, 2007 International Preliminary Report on Patentability dated Aug. 19, 2009.
PCT/US2008/053326 filed on Feb. 12, 2007 Written Opinion dated Jul. 31, 2008.
Stoeckel, Pelton, Duerig, Self-Expanding Nitinol Stents—Material and Design Considerations (ndc 2003).

* cited by examiner

STENT AND METHOD FOR MANUFACTURING THE STENT

PRIORITY

This application is a continuation of U.S. patent application Ser. No. 13/871,942, now U.S. Pat. No. 9,486,339, filed Apr. 26, 2013, which is a continuation of U.S. patent application Ser. No. 11/216,293, filed Aug. 31, 2005, which claims the benefit, under 35 U.S.C. § 119, of U.S. Provisional Application No. 60/606,261 filed Sep. 1, 2004, each of which application is incorporated by reference in its entirety into this Application.

FIELD OF THE INVENTION

The invention lies in the field of vascular stents. In particular, the invention is in the field of helical stents for peripheral arteries, the biliary tree, and other body lumens.

BACKGROUND

The vast majority of stents for use in the arterial and venous systems have been made by machining a pattern of struts and connecting elements from a metallic tubular preform (typically, by laser machining). Of these machined-tube stents, there have been two basic architectures: circumferential and helical. Circumferential configurations are based upon a series of cylindrical bands joined longitudinally by bridges to make a tubular structure. Helical configurations include a continuous helical structure (typically made of an undulating pattern of struts and end-loops) with joining structures (referred to as "bridges") joining adjacent turns of the helix to provide mechanical integrity to the tubular structure (to prevent unwinding, kinking, and buckling.

Stents have been developed for use in various lumens of the body, including the biliary tree, venous system, peripheral arteries, and coronary arteries. Stents are used to open or hold open a lumen that has been blocked (occluded) or reduced in size (stenosed) by some disease process, such as atherosclerosis or cancer. Previously developed stents for use in the biliary, venous, and arterial systems have been of two broad classes: balloon-expanded and self-expanding. In both of these classes, stents have generally been made by two different techniques: either formed from wire or machined from a hollow tube. Other manufacturing techniques have been proposed, such as vacuum or chemical deposition of material or forming a tube of machined flat material, but those "exotic" methods have not been widely commercialized.

Fine Cell Structure of Stents

Clinicians recommend the use of stents with relatively small openings to minimize the chances of friable material from the lumen wall penetrating into the interior of the stent where it may result in narrowing of the lumen by cellular proliferation or where it may embolize downstream, causing damage or ischemia. U.S. Pat. No. 6,537,310 to Palmaz et al. teaches that it is advantageous to cover a stent with a porous film having openings no larger than 17 microns in their smallest dimension to minimize the migration of embolic debris and plaque into the lumen of a stent. However, Palmaz teaches use of a stent that is very difficult to manufacture because of the great number of very small openings in the covering film or "web."

Clinicians have asked for stents with "thin, equi-spaced struts for optimal wall coverage and drug elution" ("Clinical Impact of Stent Design: Results from 10 Years Experience," C. DiMario, TCT2003). DiMario demonstrates 15.0% restenosis versus 36.6% for stents with thin struts (50 microns, Multilink) versus thick struts (average of all stents evaluated with struts greater than or equal to 100 microns). DiMario also relates stent efficacy to "integrated cell size," showing better results for the BX VELOCITY® stent with cells of 3.3 $mm^2$ versus stents with larger cell sizes. DiMario reports reduced neointimal hyperplasia for smaller struts (0.8 mm thickness for closely-spaced 125-micron struts versus 1.54 mm thickness for wider-spaced 200-micron struts). Because prior art stent designs have large gaps between stent parts, drug elution about these parts does not adequately cover all of the tissue within the bounds of the stent.

In "Clinical Impact of Stent Design: Results From Randomized Trials" (TCT 2003), A. Kastrati reports reduced residual percent-diameter stenosis after stenting (4.0% versus 5.7%) with 50-micron struts (Multi-link) versus 140-micron (Multi-link Duet).

In his report "Era of Drug-Coated and Drug-Eluting Stents" (TCT 2002), G. Grube states that the typical open-cell configuration gives poor distribution of the drug into the arterial wall because of the large open gaps when the stent is situated in a bend of the artery.

Number-of-Struts to Strut-Length Ratio

U.S. Pat. No. 6,129,755 to Mathis et al. (hereinafter "Mathis") teaches improved self-expanding stents with circumferential hoops of struts joined by oblique longitudinal bridges described therein is the importance of having a large number of struts per hoop (the number of struts counted by going around the circumference) and minimum strut length to minimize strains in superelastic materials and to prevent emboli from passing through the wall of the stent. Mathis defines a figure of merit that is the ratio of number of struts around the circumference to the length (in inches) of a strut, measured longitudinally. This ratio, which has the units of reciprocal inches, will be referred to herein as the M-D Ratio because the inventors were Mathis and Duerig. Mathis describes prior-art stents as having a ratio of about 200 and that their improved stent has an M-D Ratio of over 400. A representative stent produced by Cordis Corporation according to the Mathis-Duerig invention—referred to as the "SmartStent"—has 32 struts per circumference and shut lengths of approximately 0.077 inch, resulting in an M-D Ratio of approximately 416.

The M-D Ratio is determined by number of struts divided by strut length. For a given diameter stent, assuming "maximum-metal" configuration, which is typical for self-expanding: stents, the number of struts around the circumference is inversely proportional to the strut width. Thus, the M-D Ratio is inversely proportional to the product of strut width and length.

SUMMARY OF INVENTION

It is accordingly an object of the invention to provide a helical stent and a method for manufacturing the stent that overcome the hereinafore-mentioned disadvantages of the heretofore-known devices of this general type and that improves helical machined-tube stents, whether balloon-expanded or self-expanding.

The self-expended stent of the present invention is suitable for use in peripheral arteries, the biliary tree, and other body lumens. In particular, it will be most advantageous for use in arteries where flexure is an important factor, such as iliac arteries and carotid arteries. It is not traditional for cardiologists to use self-expanding stents in coronary arteries or coronary bypass grafts. Nonetheless, the present invention is especially suitable for the diffuse disease often encountered in these locations. Also, because of the high total surface area of the present configuration, the stent is particularly suitable for the application of drug-eluting coatings intended to reduce restenosis or for other therapies. Specifically, the stent according to the present invention allows virtually all tissue within the coverage area of the stent to be in the elution areas. In particular, the stent provides tissue coverage so that no element of wall tissue is more than 350 microns to 400 microns away from the nearest strut. Such a configuration assures a short diffusion path from a strut covered with a drug-eluting agent to any portion of the tissue.

With the foregoing and other objects in view, there is provided, in accordance with the invention, a stent, including a stent body having a circumference and struts disposed helically about the circumference in turns, at least two of the struts having respective strut ends. At least two paddle-shaped markers extend away from a respective one of the strut ends. The markers have respective marker extreme ends and different overall longitudinal lengths substantially aligning the marker extreme ends approximately along a single circumference of the stent body.

With the objects of the invention in view, there is also provided stent, including a stent body having a circumference and struts disposed helically about the circumference in turns. At least two of the struts having respective strut ends. At least two paddle-shaped markers extend away from a respective one of the strut ends. The markers have respective circumferentially flat extreme ends and different overall longitudinal lengths substantially aligning the flat extreme ends of the markers along approximately a single circumference of the stent body.

With the objects of the invention in view, there is also provided stent, including a stent body having a circumference and shuts disposed helically about the circumference in turns and having a reduced state and first expanded state defining an outer circumferential cylinder with a first circumference. At least two of the struts have respective strut ends. At least two paddle-shaped markers extend away from a respective one of the strut ends and have respective marker extreme ends. The markers have a second expanded state in which a second circumference defined by the marker extreme ends is greater than the first circumference.

In accordance with another feature of the invention, the stent body has a longitudinal axis and the single circumference is substantially orthogonal to the axis. Alternatively, the single circumference is at an angle to the axis.

In accordance with a further feature of the invention, the stent body has a longitudinal axis and the markers extend away from a respective one of the strut ends substantially parallel to the longitudinal axis.

In accordance with an added feature of the invention, the marker has a body with a first imaging characteristic, the body has at least one portion with a second imaging characteristic different from the first imaging characteristic and the first and second imaging characteristics are elected from the group consisting of ultrasound imaging characteristics, fluoroscopy imaging characteristics, x-ray imaging characteristics, and magnetic resonance imaging characteristics.

In accordance with an additional feature of the invention, the portion is a structure selected from at least one of the group consisting of a depression, a hole, a recess, a notch, a slot, a cylinder, a coating, a filling, a sphere, a texture, a porosity, a second material attached to the marker, and a particle.

In accordance with yet another feature of the invention, the marker extreme ends are substantially flat in a circumferential direction and are shaped to receive a deployment catheter.

In accordance with yet a further feature of the invention, the struts are disposed in a single helix having one strut at a proximal end of the helix and one end at a distal end of the helix.

In accordance with yet an added feature of the invention, the stent body has a proximal end and a distal end and the struts are disposed in a multiple helix with at least two helices each having one start at the proximal end and one end at the distal end.

In accordance with yet an additional feature of the invention, the multiple helix has 4 helices each having one start at the proximal end and one end at the distal end.

In accordance with again another feature of the invention, the struts are s-shaped struts and the helix has a continuous repetition of the s-shaped struts throughout a length of the helix.

In accordance with again a further feature of the invention, the struts are s-shaped struts and each of the helices has a continuous repetition of the s-shaped struts throughout a length of the helices.

In accordance with again an added feature of the invention, the struts have curved segments and the markers extend away from the curved ends.

In accordance with again an additional feature of the invention, the markers are combinations of radiopaque, ultrasound, and magnetic resonance imaging markers. The radiopaque markers can be tungsten, tantalum, molybdenum, platinum, gold, zirconium oxide, barium salt, bismuth salt, hafnium, and/or bismuth subcarbonate. The ultrasound markers can be abrasions, holes, voids, porous materials, porous coatings, hollow balloons, and/or layered materials having different sonic properties. In particular, the ultrasound m:u•ker can be a hole 0.50 millimeters in diameter filled with a composite of glass microballoons and tungsten powder suspended in an epoxy matrix. The magnetic resonance imaging markers can be of paramagnetic, diamagnetic, and ferromagnetic materials. The magnetic resonance imaging markers can be of gadolinium, gadolinium salts, gadolinium foil, gadolinium powder, hematite, oxides, nanocrystalline iron oxide, and/or iron powder. The ultrasonic markers can be of glass or ceramic microballoons.

In accordance with still another feature of the invention, one of the markers has a relatively shorter extension portion adjacent an end of the helix turn and others of the markers have a relatively larger extension portion increasing in size along the helix turn in a direction away from the relatively shorter extension portion.

In accordance with still a further feature of the invention, the markers have paddle portions with aligned ends.

In accordance with still an added feature of the invention, the stent body has a longitudinal axis and the markers have paddle portions with ends opposite the extension portions defining a circumferential plane substantially orthogonal to the longitudinal axis.

In accordance with still an additional feature of the invention, the extension portions have a given width in a circumferential direction of the stent body and the paddle portions have a width in the circumferential direction greater than the given width.

In accordance with another feature of the invention, the extension portions have a given width in a circumferential direction of the stent body and the paddle portions have a width in the circumferential direction equal to the given width.

In accordance with a further feature of the invention, the paddle portions are non-circular.

In accordance with an added feature of the invention, the extreme ends of adjacent ones of the markers are separated by a distance no greater than 18 microns.

In accordance with a concomitant feature of the invention, the struts have a reduced state and first expanded state defining an outer circumferential cylinder with a first circumference, at least two of the struts have respective strut ends, at least two of the paddle-shaped markers extend away from a respective one of the strut ends and have respective marker extreme ends, and the markers have a second expanded state in which a second circumference defined by the marker extreme ends is greater than the first circumference.

The present invention relies on a helical configuration with much shorter struts and significantly higher number of struts around the circumference than the prior art. Indeed, helical stent configurations according to the present invention are not limited to even-integral numbers of struts—as are "hoop" configurations taught by Mathis. In fact, odd-integral numbers of struts around the circumferential or even non-integral numbers of struts around the circumference are possible in the helical configuration of the present invention because there is no requirement for the struts to rejoin themselves to make complete hoops. In other words, a helical stent could have 31.567 struts per revolution, or any other arbitrary number. Mathis teaches that increasing the M-D ratio increases the rigidity of a stent, yet the rigidity of two comparative stents bears this relationship only if the stents being compared are expanded to comparable opening angles between the struts. In fact, with commercially available stent product lines produced to the M-D configuration, stents of different diameters frequently have the same number of struts. Even so, such a configuration family has smaller opening angles in smaller sizes than in larger sizes; this is because similar stent preforms are used to make a range of final stent sizes. The smaller stents in a product family sharing the same preform configuration (including the number of struts) have smaller opening angles, of course, resulting in lower chronic outward force (COF) and lower radial resistive force (RRF) to collapse, because the effective bending-lever length is longer in struts with lower opening angles. Mathis teaches M-D Ratios of over 400 and numbers of struts up to 32 or more but does not teach or suggest ratios of near or over eight-hundred (800), let alone over one thousand (1000). Mathis, specifically, does not mention what effects a much larger number of struts would have, and does not imply implementation of significantly shorter struts.

In the present invention, an exemplary configuration for an 8 mm diameter stent incorporates 46 struts around the helical circumference and the struts have a length of approximately 0.99 mm (0.039 inches). The M-D Ratio for this exemplary configuration according to the present invention is, therefore, 1180—nearly three times the ratios taught in the prior art. Stents according to the present invention have new and unexpected properties, even though they require greater attention to opening angles (and, hence, have a more limited useful size range for a given configuration).

In comparison with prior art stents having cells of 3.3 $mm^2$, the present invention gives an integrated cell size of 1.6 $mm^2$ per cell unit in an 8 mm diameter stent. In a configuration with bridges every three cell units, the total integrated cell size would be 4.8 $mm^2$, which is proportionately smaller than that of the BX VELOCITY® 3 mm stent.

Specifically, configurations according to the present invention have much smaller openings when expanded and, particularly, when the expanded stent is flexed in bending. The substantially smaller openings result in greatly improved resistance to the passage of emboli through the stent wall.

Another characteristic of stents according to the present invention is a greatly increased flexibility and resistance to buckling in bending or torsion. Stents according to the present invention also have improved fatigue life in real-life applications, resulting from a large number of struts and bending segments to absorb irregular, localized deformations caused by the anatomy—as opposed to such local deformations being placed on a small number of struts and bending segments, which results in over-straining some of these elements.

Stent configurations optimized for a particular expanded diameter will have struts as wide as possible, consistent with the maximum allowable strain during storage and compression. The result of such a criterion is that stent configurations according to the present invention, with a greater number of struts of shorter length and narrower width than prior art configurations, will allow greater bending deflections, resulting in greater possible opening angles. Constructing an expanded stent with greater allowed opening angles also results in a relatively shorter projected lever-arm length acting on the struts and bending segments when the stent is expanded in the anatomy. These shorter lever arms result in higher outward forces applied to the vessel walls when the stent is expanded.

It should be noted that the present invention results in configurations that are optimized for a small range of expanded sizes, creating the need to have individualized configurations for each expanded size of stent. This approach deviates from the prior art and results in higher configuration and validation costs, but results in stents with significantly improved flexural and fatigue properties while, at the same time, providing optimized radial outward forces and collapse resistance for each size.

Another characteristic of stents made according to this invention is the increased difficulty of collapsing the stent when preparing it for insertion into a delivery catheter. The struts of stents made according to the present invention are proportionately narrower and, hence, less stiff in bending (in proportion to the cube of the width of the shuts) when compared to prior art stent designs. This decrement in stiffness may be offset by increasing the opening angle of the stent, as described elsewhere herein, but the reduced stiffness of the struts (and also the increased opening angles) results in a tendency for portions of the helix to buckle when subjected to the stresses and strains required to fully collapse the stent prior to insertion into its delivery system. The result of this buckling is that a series of struts and loops forming a portion of the helical winding will resist collapsing uniformly along the helical axis, but rather buckle away from the helical axis (usually remaining in the plane of the cylindrical surface of the stent). When a portion of the helix buckles, the struts of that turn may begin to interfere or interdigitate with the struts of an adjacent helical turn. Thus, stents made according to the present invention are more difficult to compress into their delivery system.

This tendency for a series of struts and loops to buckle away from the helical axis is aggravated when the struts are very narrow, when the opening angles are higher, and when there is a long series of struts between the connecting bridges. The presence of the connecting bridges that join adjacent turns of the stent stabilizes the stent during compression; this stability is greater when there are only a few struts between bridges, and the stability is reduced when there is a large number of struts between bridges. For example, stents made with series of seven or nine struts between bridges have a high tendency toward buckling when compressed; stents made with five struts between bridges have an intermediate tendency toward buckling when compressed; and, stents with only three struts between bridges have a low tendency toward buckling when compressed. It should be noted that this tendency toward buckling does not adversely affect the characteristics of the stent when expanded in the body, because the compressive strains experienced in the body are insufficient to cause the buckling seen during compression into the delivery system. However, it has been found that stents with very low numbers of struts between bridges (e.g., one or three), though they are very easy to fully compress, do not have flexibility as great as that of stents with larger numbers of struts between bridges (e.g., seven or nine). As a result, it has been found that there is a tradeoff between design choices which create a stent that is easy to compress versus choices which make the stent flexible. It has been found that stents made according to this invention, configured with an M-D ratio in the range of 1000, have the most favorable balance of flexibility and buckling during compression when the number of struts between bridges is in the range of three to five.

Other features that are considered as characteristic for the invention are set forth in the appended claims.

Although the invention is illustrated and described herein as embodied in a helical stent and a method for manufacturing the stent, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

Figure 1:
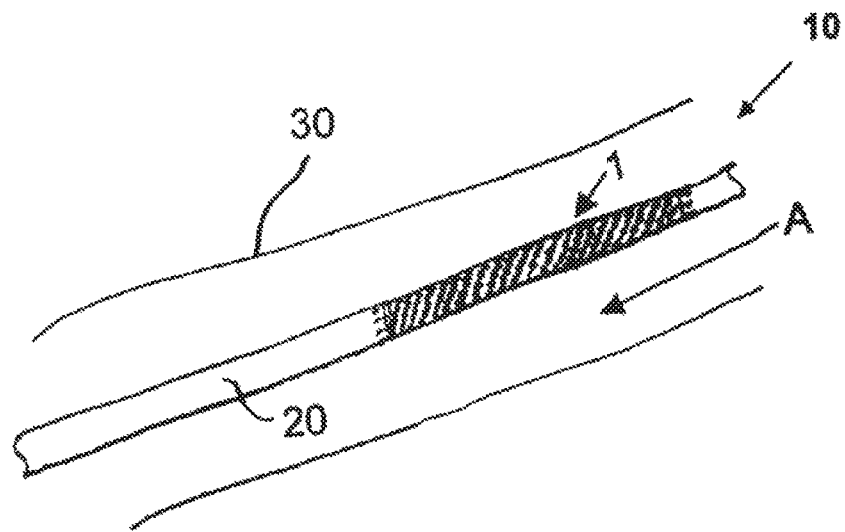
FIG. 1 is a fragmentary, enlarged partially cross-sectional and partially plan view of a stent delivery system configured to implant a stent according to the invention in a vessel.
Figure 2:
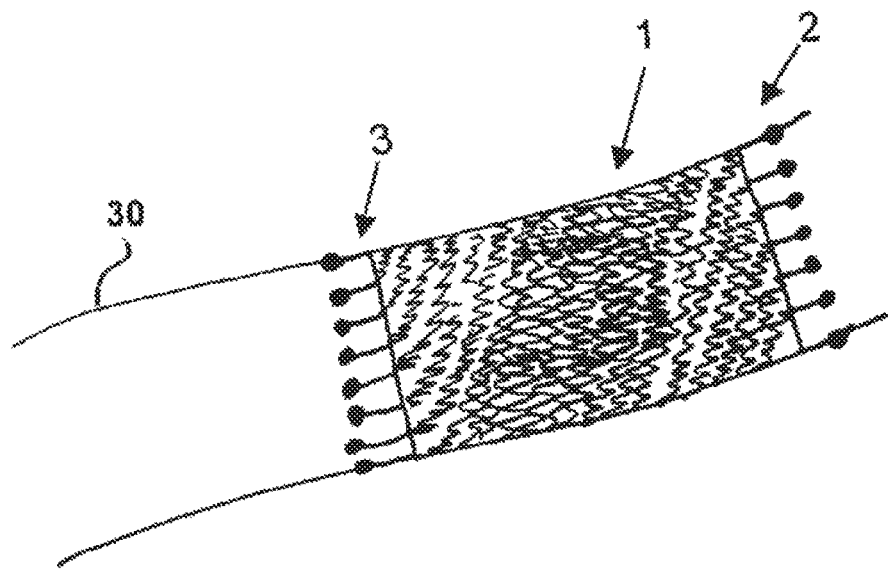
FIG. 2 is a fragmentary, enlarged plan view of the stent of FIG. 1 expanded and implanted in the vessel.

Referring now to the figures of the drawings in detail and first, particularly to FIG. 1 thereof, there is shown is a helical stent 1 according to the present invention fitted on a delivery catheter 20 of an exemplary delivery system 10. The helical stent 1 is about to be implanted in a vessel 30. The helical stent 1 is in its unexpanded state and loaded into/onto the delivery system 10 that has traveled to an implantation site. FIG. 2 illustrates the helical stent 1 implanted in the vessel 30 after being expanded, whether by a balloon of the catheter 20 or by self-expansion due to a shape memory of the material of the stent 1.

The helical stent 1 has proximal 2 and distal 3 ends—defined by a blood flow direction A. The helix of the stent 1 can be a single coil with one start at the proximal end that winds all the way to the distal end. Such a configuration is possible with the present invention because the helical stent 1 has very short struts, which will be explained in further detail below. Another configuration alternative usable with short struts is a multiple-helix configuration (shown in FIG. 2), where more than one helixed start is present, for example, a double-lead, a triple-lead, and so on. With an exemplary 8 mm size of the helical stent according to the present invention, up to 4 leads are practical.

Figure 3:
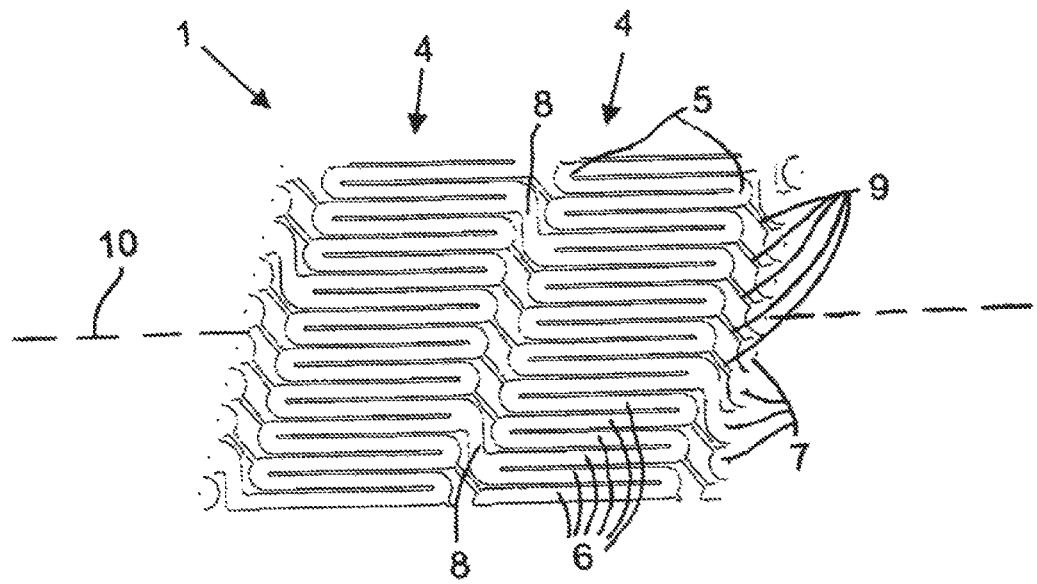
FIG. 3 is a fragmentary, enlarged plan view of a portion of a first embodiment of the stent of FIG. 1.
Figure 4:
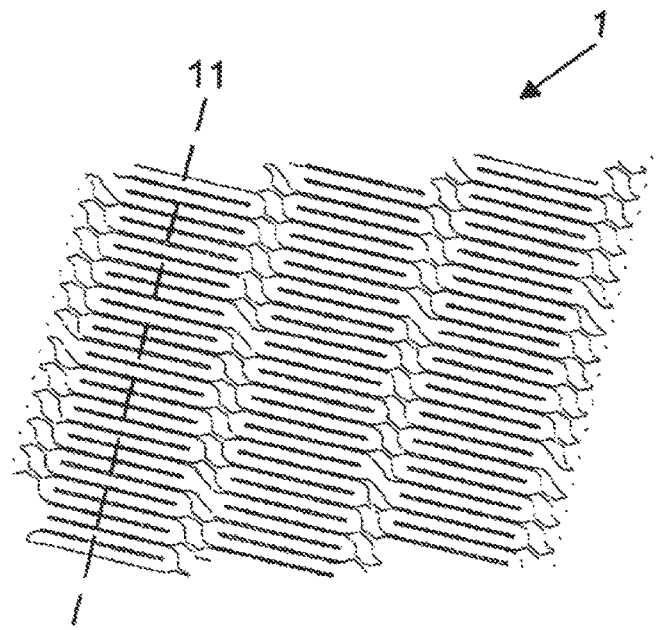
FIG. 4 is a fragmentary, enlarged plan view of a portion of a second embodiment of the stent of FIG. 1.

FIGS. 3 and 4 show enlarged views of a portion of the body of the helical stent 1 of the present invention. Each turn 4 of the helix is formed, in a preferred embodiment, by a continuous repetition of s-shaped struts 5 throughout the length of the helix. The struts 5 have straight portions 6 and curved portions 7 connecting respectively adjacent straight portions 6. Connecting bridges 8 have a width substantially similar to a width of the straight and curved portions 6, 7 and connect adjacent turns 4 of the helix. Also connecting adjacent turns of the helix are sacrificial bridges 9, which have a width smaller than a width of the straight and curved portions 6, 7. Both of the bridges 8, 9 will be described in greater detail below.

Stents 1 may be made according to the present invention with struts 5 that are aligned with the longitudinal axis 10 of the stent 1, as shown in FIG. 3, or the struts 5 may be aligned perpendicular to the helical direction 11, as shown in FIG. 4. There are advantages and differences to both configurations. The longitudinally aligned straight portions 6 of the struts 5 produce a stent 1 that requires lower force to deploy from a confining sleeve because there are no oblique, twisting, knife-edges to cut into or grip the sleeve. One characteristic of this embodiment, is that the struts 6 are not of equal length (there is an equal number of short and long struts) and, therefore, it is not possible to fully balance the flexibility of these struts to fully utilize the properties of the material used to build the stent 1. In comparison, the configuration shown in FIG. 4 with helically aligned straight portions 6 of the struts 5 has the advantage of equal strut lengths. This configuration, in comparison, has a higher friction when the stent 1 is engaged inside a deployment system.

Other advantages and differences exist for these two configurations, including ease of manufacture, ease of inspection, and stability during expansion or deployment of the longitudinal and helically aligned strut configurations. But, either may be used to practice the teachings of the present invention.

Lollipop Crown and Retention Levers

It is customary to provide radiopaque markers on stents so that they can be easily visualized by using x-rays for assisting their placement and deployment. The present invention provides a convenient area at which to locate these markers, specifically, beyond the ends of the helical pattern of struts. If the markers 12 are paddle-shaped (that is, having a substantially disk-like enlarged portion with a narrow extension that joins it to the structure of the stent), they may be attached to the ends of the 180-degree bending segments 7 (or to other locations on the bending segments 7 or straight portions 6). It is advantageous to dispose the markers so that a paddle with a short extension is located near the end of the helix (the extreme end of the helical pattern) and paddles on longer connectors are located at other locations around the circumference. In such a configuration, the extreme ends of the paddles are even, providing a relatively planar end to the stent 1. However, the marker portions 12 need not be paddle-shaped. They can merely be rod-shaped to extend away from either or both of the distal and proximal ends 2, 3 of the stent 1. These rods can be expanded for better seating in the vessel and, even with a smaller surface area as compared to the paddle-shaped markers, can still provide sufficient area for receiving indicators that allow for better imaging.

Figure 6:
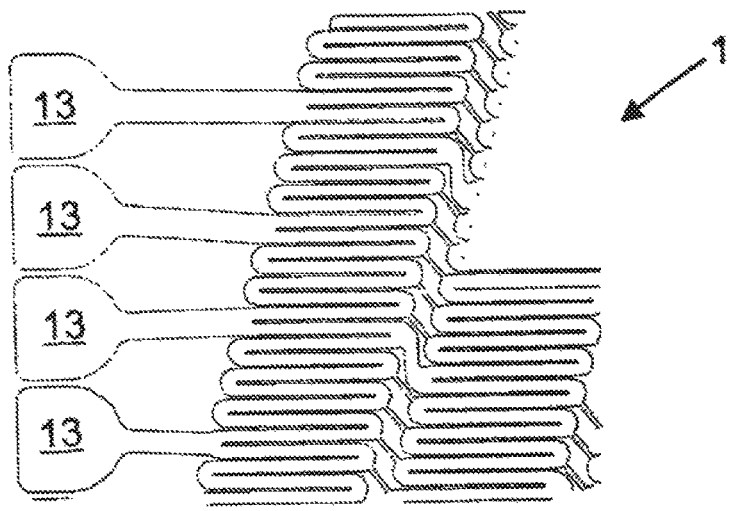
FIG. 6 is a fragmentary, enlarged plan view of a portion of the first embodiment of the stent of FIG. 3 with flat-ended markers.

The flat end provided by the paddle-shaped markers 12 of FIG. 6, for example, facilitates pushing the stent 1 out of a deployment device (although a shaped pusher that conforms to the helical end of the stent could be used but is harder to manufacture and align). During deployment of a self-expanding stent, a pusher component of a delivery catheter exerts a (distally-directed) counter-force onto the proximal end of the stent while a covering sleeve is retracted from its position over the stent. As the covering sleeve is retracted relative to the stent and the pusher, the distal end of the stent is exposed and, therefore, expands to contact the interior of the vessel. Thus, it is important for the pusher to be able to apply evenly the distally directed force onto the proximal end of the stent during deployment. Also, for most medical indications, physicians prefer stents with flat ends substantially perpendicular to the longitudinal axis of the device so that there is an even transformation from the end of the stent to the unsupported (unstented) portion of the vessel wall.

Figure 5:
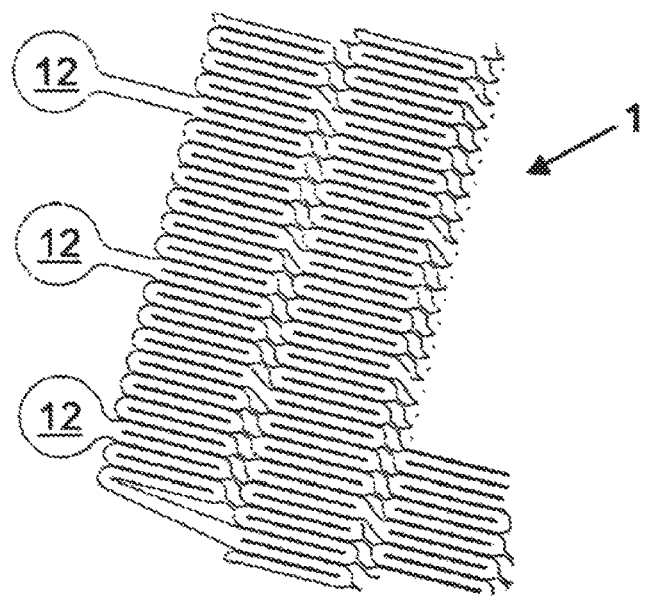
FIG. 5 is a fragmentary, enlarged plan view of a portion of the second embodiment of the stent of FIG. 4 with circular markers.

The paddle shaped markers 12 described above can be spaced from the helical end of the stent by narrow connectors as shown in FIGS. 5 and 6, or by full-width connectors (i.e., markers that are of uniform width from their ends to the point where they join the struts or loops of the stent), or by directly connecting them to the other elements of the stent. FIG. 5, for example, illustrates three paddle-shaped markers 12 attached by narrow connectors to the helical end of a portion of a stent 1.

While the disk-like enlarged portions of paddle-shaped markers 12 can be rounded, it is preferable for the extreme outer ends to be relatively straight. As such, the paddle-shaped markers 12 may be provided with non-circular ends 13 to facilitate engagement of the pushing device of the deployment-catheter with which the stent is implanted. For example, FIG. 6 shows flat-ended paddle-shaped markers 12 that maximize contact between the paddles and the pushing device.

In addition, the paddle-shaped markers 12 may be used to help anchor the stent 1 during and after deployment. Specifically, the paddles may be radially expanded further than the struts 5, 6, 7 so that they form a funnel-shaped end to the stent 1 once expanded.

While the present drawings show paddle-shaped markers without separate radiopaque inserts, it should be noted that pieces of radiopaque materials, such as tungsten, tantalum, molybdenum, platinum, or gold, might be inserted into the markers to enhance their visibility under x-rays. For example, inserted cylinders of tantalum 0.50 millimeters in diameter and having a thickness equal to or less than that of the marker paddles, may be pressed, glued, riveted, threaded, or otherwise attached into holes or depressions formed in the paddles.

Circumferential Bridges and Fixation Structures

Figure 7:
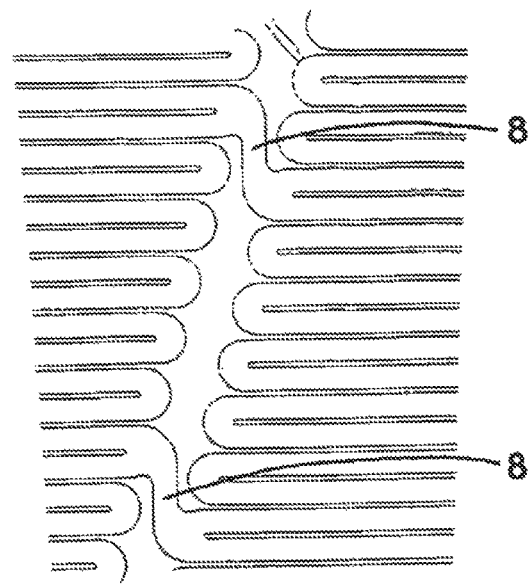
FIG. 7 is a fragmentary, enlarged plan view of a further enlarged portion of the first embodiment of the stent of FIG. 3 with some sacrificial bridges removed.
Figure 8:
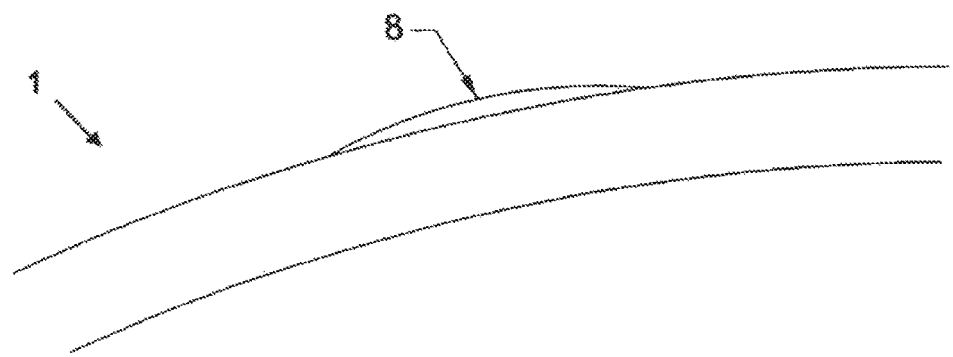
FIG. 8 is a fragmentary, side elevational view of a portion of an expanded stent according to the invention with a protruding bridge.

According to the present invention, there is an array of connecting bridges 8 that connect adjacent turns or columns of struts 4 to provide the desirable overall stent flexibility as well as structural integrity. It is advantageous to form these bridges 8 in a substantially circumferential direction, as shown in FIG. 7. Two advantageous characteristics emerge by so forming the connecting bridges 8. First, the vertical (circumferential) offset caused by the bridges 8 ensures that, after expansion, the adjacent 180-degree bending segments (the vertices of the expanded strut pairs) are offset from one another and, thus, will interdigitate, allowing the stent 1 to bend easily. Second, these circumferential bridges 8 are curved sharply in the plane perpendicular to the axis 10 of the stent 1, which curvature results from the stent 1 being formed from small-diameter tubing. By careful control of the expansion process, it is possible to expand the stent 1 while retaining substantially all of the curvature of these bridges 8. In the resulting expanded stent 1, these bridges 8, then, extend radially away from the cylindrical surface of the stent 1 and present edges perpendicular to the axis 10 of the stent 1. Thus, during and after implantation, these features engage the vessel or body lumen wall 30, preventing migration of the stent 1. The enlargement of a bridge 8 in FIG. 8 illustrates how these structures protrude beyond the wall of a stent 1 in this manner.

Multi-Mode Markers for Ultrasound, X-Ray, and MRI

Customarily, radiopaque materials such as gold, tantalum, zirconium oxide, barium and bismuth salts, hafnium, molybdenum, etc., are attached to stents to enable visualization by x-rays. The present invention is suitable for incorporating such markers, especially at the location of the paddles 12, 13, as described above.

In addition to the prior-art use of radiopaque markers, it is possible to use other types of fiducial markers to enable placement, deployment, and subsequent location and diagnosis of the stent 1. Specifically, other non-illustrated markers can be made that are easily imaged by ultrasound, such as abraded surfaces, holes, voids, porous materials and coatings, hollow balloons, and layered materials of different sonic properties, to name a few. For example, a hole 0.50 millimeters in diameter may be filled with a composite consisting of glass microballoons and tungsten powder suspended in an epoxy matrix. Such a composite marker would be highly visible under ultrasound imaging as well as x-ray imaging. Additionally, markers having varying textures have improved anchoring characteristics.

Magnetic resonance imaging may be enhanced by inclusion of paramagnetic, diamagnetic, and ferromagnetic materials that locally change the magnetic-field-producing spinenergy transitions in odd-number nuclei such as hydrogen, carbon-13, flumine-19, and other nuclides known to those skilled in the art of magnetic resonance imaging. Specifically, small pieces of gadolinium or gadolinium salts (paramagnetic) provide visible changes to the image formed by hydrogen nuclei in their vicinity, thus, such materials can be incorporated into fiducial markers. Nanoscale ferromagnetic materials, such as hematite or other oxides, can also provide useful MRI artifacts without troublesome image distortion.

Magnetically active elements, salts, and compounds can be incorporated individually or in combination with other marker materials, such as radiopaque materials or ultrasound-visible structures or materials, to make multi-mode markers. Composite markers may contain materials with magnetic properties suitable to present fiducial marks on images made by magnetic resonance imaging (MRI) as well as other imaging modalities. Examples include combinations of radiopaque materials (such as, tungsten powder, zirconium oxide, bismuth subcarbonate, and gold powder), magnetically active materials such as diamagnetic or ferromagnetic materials (including gadolinium foil and powder, gadolinium salts, nanocrystalline iron oxide, and iron powder, for example), and ultrasonically visible material such as glass or ceramic microballoons.

Manufacturing

The standard method for manufacturing machined tubular metal stents is to begin with a small-diameter metallic tube, typically, of stainless steel, platinum alloy, or chromium-cobalt alloy for balloon-expanded stents and of a nickel-titanium alloy for self-expanding stents. This tubing is mounted in a laser machining system that rotates the part around a stationary axis so that the focal point of a laser beam impinges upon the surface of the tube. When laser power is applied along with a coaxial jet of gas (either air, oxygen, or an inert gas such as argon), the material is perforated by the laser energy (and possibly assisted by chemical reaction with air or oxygen). The tubing is moved under the laser beam in at least two axes, rotational and longitudinal, so that a continuous cut (or kerf) is made while the laser energy is applied. The laser beam is switched on and off under computer control in coordination with the longitudinal and rotational motions so that a discontinuous pattern of cuts is applied to the tubing.

Following the laser-cutting operation, excessive material is removed from the interior and exterior surfaces of the tubing, and the tubing is further processed to produce either a balloon-expandable or a self-expanding stent. In the case of a balloon-expandable stent, the laser-cut tubing preform is polished and cleaned using a combination of chemical, mechanical, and electrochemical measures to produce a finished stent that is, then, for example, crimped onto a balloon catheter. In the case of a self-expanding stent, the laser-cut tubing is expanded by forcing it onto a succession of larger and larger mandrels. At each step of expansion, the tubing is subjected to an appropriate heat-treating step to thermally set the expanded step. For example, nickel-titanium tubing may be heat treated at 480 degrees Celsius (480°. C./896° F.) for thirty seconds while expanded on a mandrel to set that stage of expansion. Typically, two to six expansion stages are necessary to fully expand a nickel-titanium self-expanding stent. After expansion, the stent is finished by a combination of chemical, mechanical, and electrochemical polishing to produce a smooth, biocompatible surface suitable for implantation. The finished stent is, then, chilled (to transform it to the soft and deformable martensitic condition) and compressed radially to a size small enough to be placed into catheter of the stent delivery system.

The Importance of Uniform Expansion During Manufacturing

One manufacturing problem that must be overcome with self-expanding stents having the fine structures as described in the present invention is uneven opening occurring during thermo-mechanical expansion of the as-cut tubing to the final, expanded stent. The standard manufacturing process involves stretching the laser-cut stent over progressively larger tapered-end cylindrical mandrels and heat-treating the material at several stages while supported by these mandrels. The stent can be expanded by stretching it onto the successive expansion mandrels either at a low temperature (in the soft, martensitic condition) or at ambient temperature (in the springy, austenitic condition). Once expanded onto a mandrel, the stent is exposed for a short period (several seconds to a few minutes) of high temperature, typically in the 450 to 500 Celsius range, to "shape-set" or anneal the stent at that level of expansion.

While the expansion process has been well understood by stent manufacturers in the past, it is problematic because great care must be exercised to make sure that no portion of the stent is over-strained (over-stretching or over-bending) during the stages of expansion. Overstraining can damage permanently the superelastic material of which the stent is formed (typically a nickel-titanium superelastic alloy), resulting in hidden defects within the material that might cause immediate fracture or, worse, fatigue failure after the stent has been implanted. Therefore, manufacturers typically expand stents in several fractional steps, and may employ elaborate measures, either by human skill or tooling, to prevent any portion of the stent from being over-strained. Over-straining is most commonly seen as a pair of struts having an unusually large opening angle at their vertex relative to the angle of other strut pairs in the vicinity. This condition must be controlled and identified by in-process inspection because it may be hidden by later expansion steps and because it is an inherently unstable condition. That is, during a given expansion step, once a pair of struts begins to open excessively, that vertex becomes weakened, and the opening strains tend to be further concentrated on that particular pair of struts, so that it becomes progressively more over-strained.

Sacrificial Bridges

The present invention provides a process for preventing this local over-straining. In the present invention, as compared to the original number of bridges 8, 9 originally existing between adjacent columns (or helical turns) of strut pairs in the unfinished stent, only a few bridges 8 exist in the finished stent, which remaining bridges 8 provide the desired flexibility and resistance to fatigue. In the as-cut condition and during the steps of expansion, additional sacrificial bridges 9 connect the bending segments joining strut pairs in adjacent turns or columns. Thus, when the stent 1 of the present invention is being expanded, it has greatly improved robustness, and each pair of struts is connected at the maximum number of points to adjacent parts of the expanding stent. What is referred to herein as sacrificial bridges 9 provides these additional connections and causes the expansion strains to be much more evenly shared by all the elements of the stent, which sharing results in a significant increase in the evenness of strains during expansion. The result is an expanded stent with vertex opening angles that have much less variation.

It is true that the sacrificial bridges 9 substantially reduce the flexural (bending) flexibility of the stent 1. Thus, they must be removed prior to finishing the stent 1. These sacrificial bridges 9 may be removed at any stage after expansion, but, preferably, they are removed immediately after the final expansion heat-treating step, prior to any material-removal or polishing steps, so that any burns left by removal will be reduced or eliminated during the polishing steps. Alternatively, the sacrificial bridges 9 may be removed after some of the expansion stages, but prior to one or more final expansion stage because it has been found that, once the stent 1 has been partially expanded in a very even manner, subsequent expansion steps do not generally introduce unevenness among the opening angles. In any case, it is only necessary to remove the extra, sacrificial bridges 9 at some point prior to implantation so that the finished stent 1 has the desired flexibility in its final, implanted form.

Bridge Removal Processes

Figure 9:
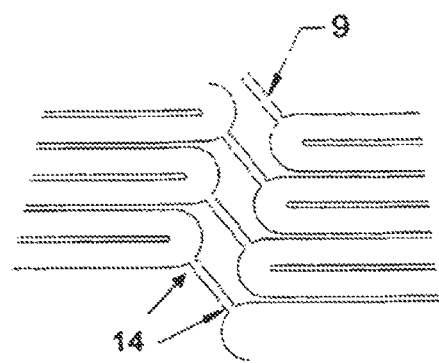
FIG. 9 is a fragmentary, enlarged plan view of a further enlarged portion of the first embodiment of the stent of FIG. 7 with the sacrificial bridges having break points.

To facilitate removal of the sacrificial bridges 9, special features can be engineered into the as-cut structure to provide prescribed locations for cutting or breaking the sacrificial bridges 9. These features are illustrated in FIG. 9 as, for example, notches 14 formed at one or both of the ends of the sacrificial bridges 9 connected to the struts of adjacent turns 4. While providing notches 14 is only one example to form the cutting/breaking location, alternative exemplary methods of removing sacrificial bridges include chemical etching, abrasive blasting, grinding, electrochemical etching or polishing, shearing, or laser cutting.

Final Burr Removal Processes

Customarily, stents are finished by a combination of abrasive blasting, glass-bead honing, chemical etching, mechanical polishing, and electrochemical polishing. All of these processes assist removal of any remaining burr left by the removal of the sacrificial bridges 9. In addition, other measures, such as grinding, shearing, mechanical polishing, and cutting may be used to locally smooth and remove buns left by the sacrificial bridges 9.

Figure 10:
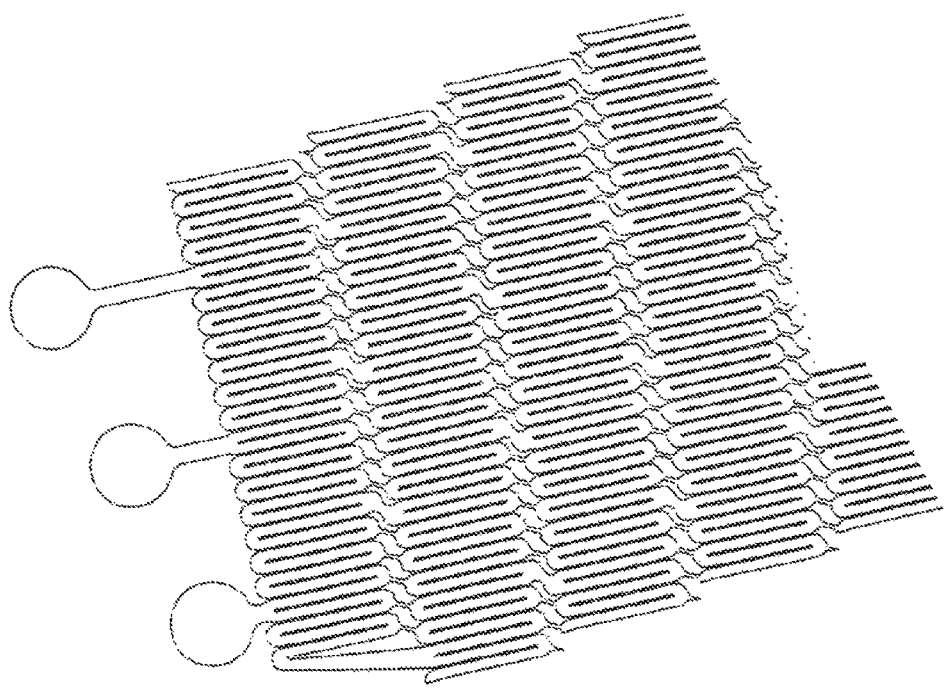
FIG. 10 is a plan view of a flat cut pattern representing the laser-cutting path to be created around a circumference of tubing from which the stent according to the invention is to be created.
Figure 11:
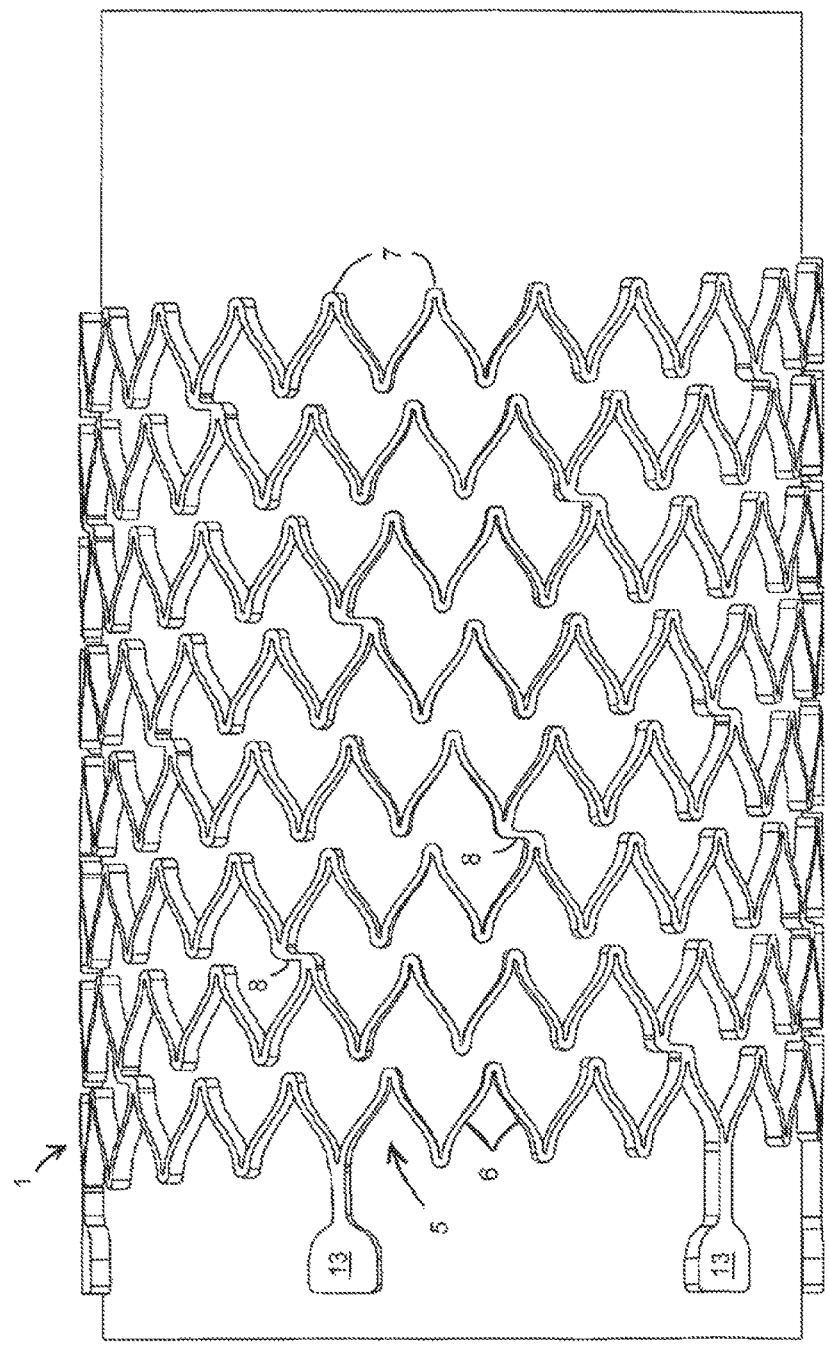
FIG. 11 is a fragmentary, enlarged, perspective view from the side of a stent according to the invention.
Figure 12:
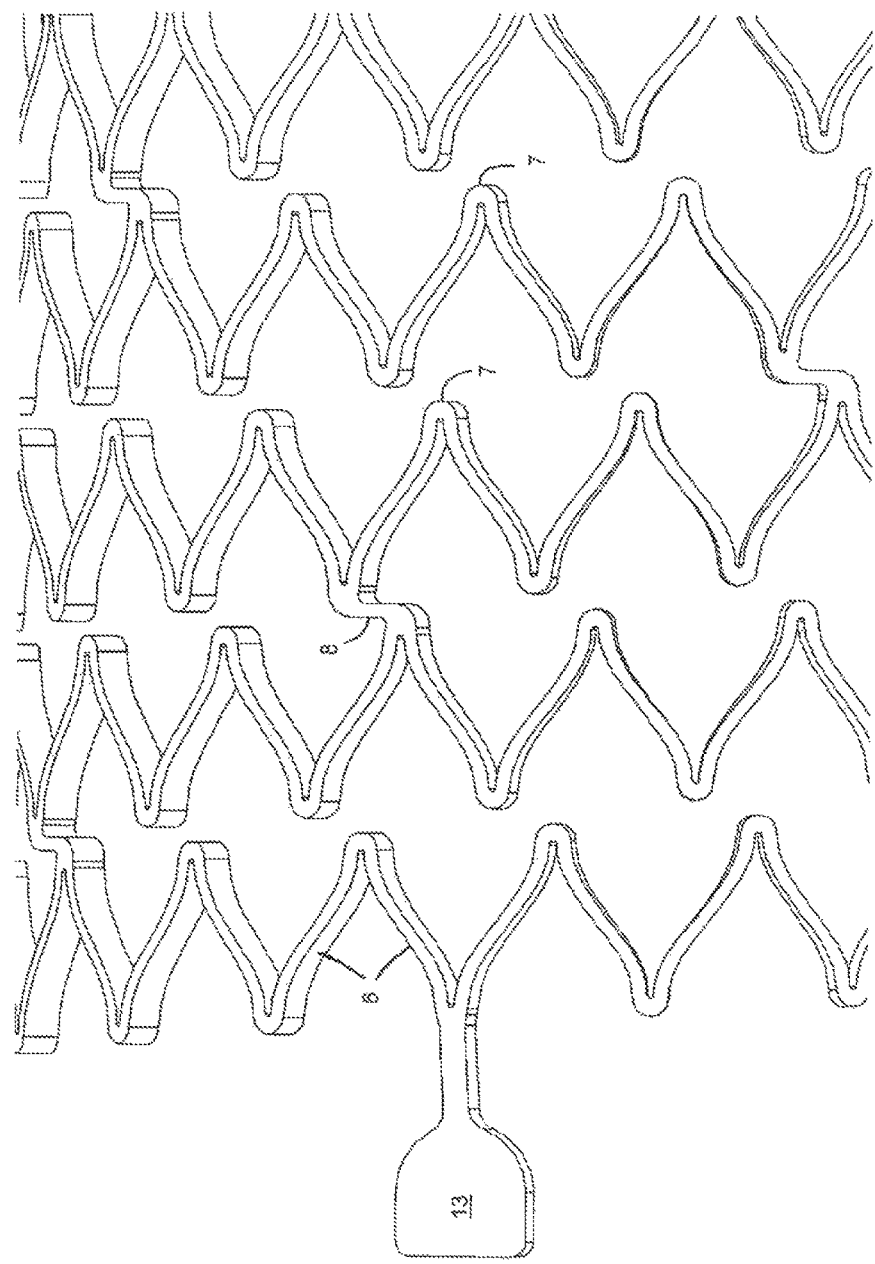
FIG. 12 is a fragmentary, further enlarged, perspective view of a portion of the stent of FIG. 11.
Figure 13:
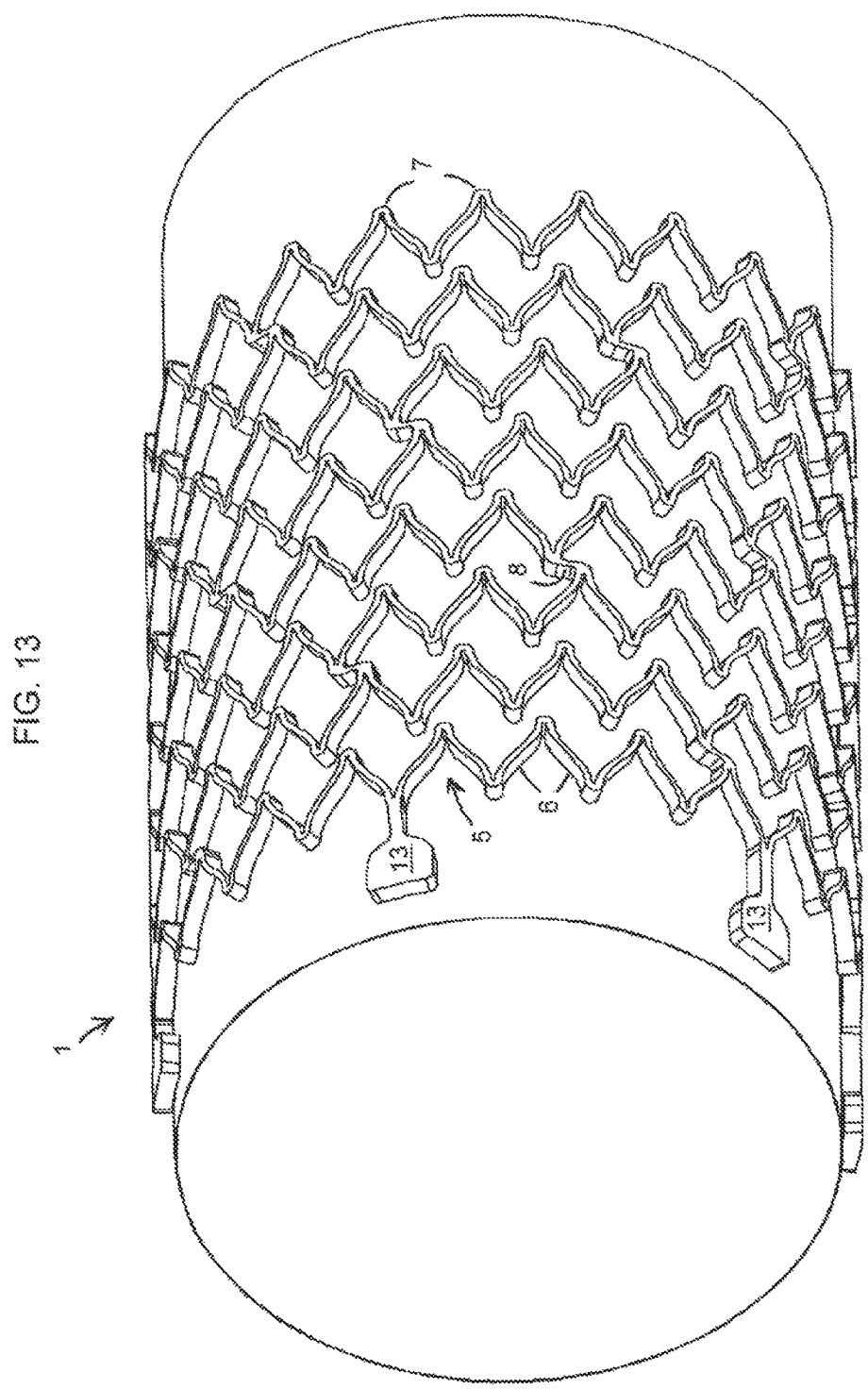
FIG. 13 is a fragmentary, enlarged, perspective view from an end of the stent of FIG. 11.
Figure 14:
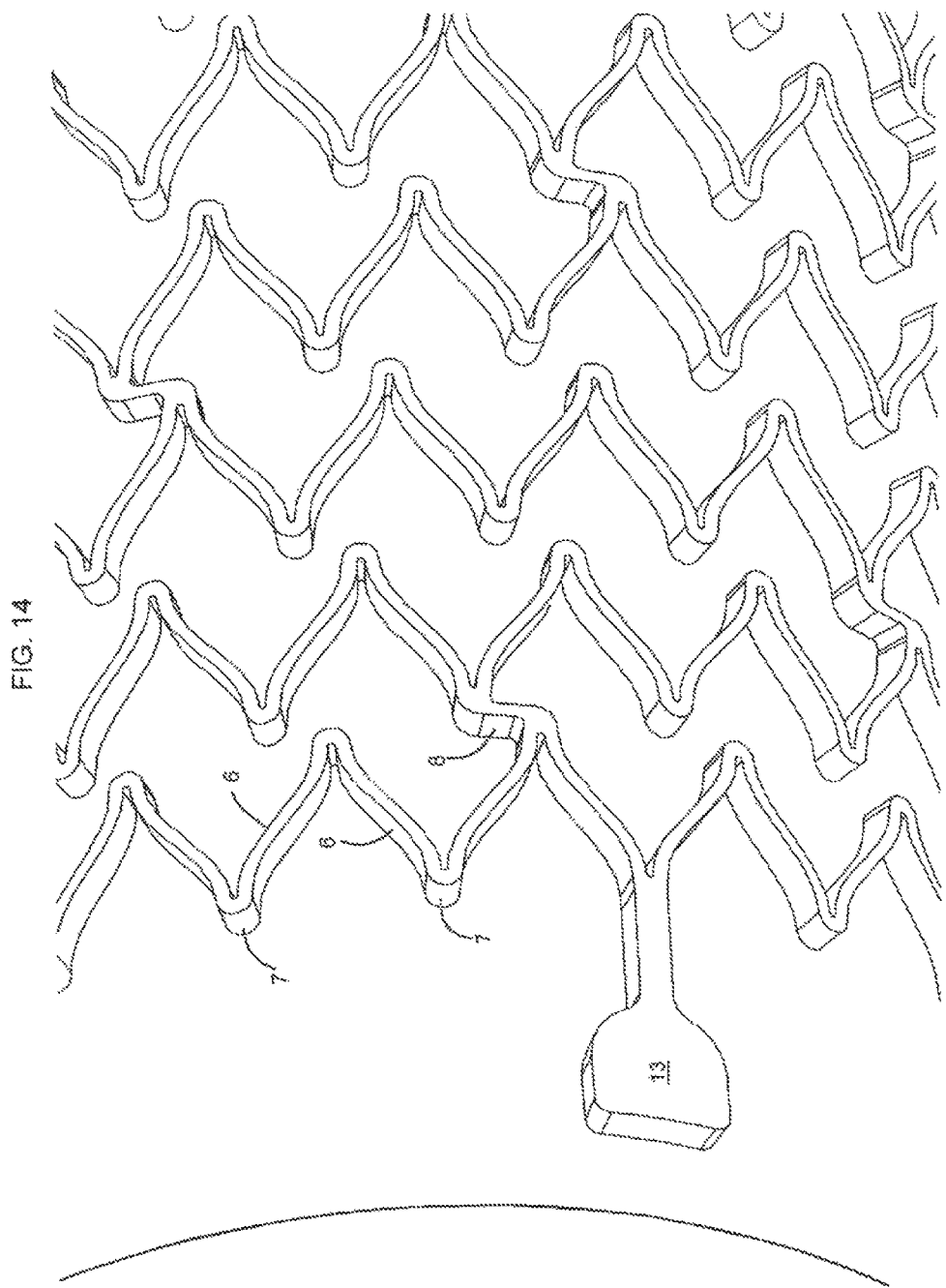
FIG. 14 is a fragmentary, further enlarged, perspective view of a portion of the stent of FIG. 13.

FIG. 10 illustrates a flat cut pattern representing the laser-cutting path that will be created around the circumference of tubing from which the stent 1 is to be made. For clarity, the pattern in FIG. 10 is broken along a longitudinal line to represent it as a flat, two-dimensional pattern. In practice, however, this two-dimensional flat pattern (representing width and length) is transformed into a two-dimensional cylindrical pattern (representing rotation and length) by the programming of the computer-controlled laser-cutting machine so that the cut pattern is arrayed continuously around the cylindrical surface of the tube. The resulting cut pattern produces a cylindrical or helical array of struts 5 to form the stent 1.

FIGS. 11 to 14 illustrate a portion of a stent 1 according to the invention with the s-shaped struts 5 oriented in the configuration shown in FIG. 3, i.e., the straight portions are substantially aligned with the longitudinal axis of the stent 1 before expansion. In FIGS. 11 to 14, the right end of the stent is not depicted and the left end is shown with flat-ended markers 13 extending from respective curved portions 7. The narrow portions of the markers 13 do not have the same length and, therefore, the extreme left flat ends of the markers 13 align along a single planar surface orthogonal to the longitudinal axis of the stent 1 once the stent is expanded. The embodiment of FIGS. 11 to 14 shows the stent 1 in an expanded state after the sacrificial bridges 9 have been removed. As can be seen in each of FIGS. 11 to 14, the bridges 8 align along a circumference of the interior cylinder defined by the stent 1. The exemplary embodiments of FIGS. 3 to 7 and 9 to 10 show the helical direction 11 of the struts 5 as "left-handed" (the helical direction 11 advances helically to the left) and the advancing direction of the bridges 8, 9 as "right-handed" (the advancing direction of the bridges 8, 9 is opposite the helical direction 11). The exemplary embodiment shown in FIGS. 11 to 14, in comparison, shows the helical direction 11 as right-handed and the direction of the bridges 8, 9 as left-handed. The interior cylinder depicted in FIGS. 11 to 14 is only presented for illustrative purposes.

Using Very Narrow Kerfs in Stents with High Strut Count

It has been discovered that the manufacture of the stent 1 according to the present invention, in particular, the laser cutting and expansion steps, are made substantially more difficult when the size of struts 5 is reduced and the number of struts 5 is increased. For example, it has been found that normal laser cutting processes yield a finished kerf width (after material removal processes needed to provide a stent with the desired polished finish) of approximately 25 to 40 microns. If, for example, a total of 46 struts were disposed around a circumference, then the total circumferential width of kerfs would be at least 46×25 microns, or 1150 microns (1.15 millimeters). Of this kerf space, half is not collapsible during compression of the stent, because half of the kerfs are at the inside of the 180-degree bends that join the ends of the struts. Hence, a stent of the current configuration made by conventional manufacturing processes has at least 0.57 millimeter of incompressible circumference resulting from the kerfs at the 180-degree bends (corresponding to 0.18 millimeter of diameter reduction). However, by reducing the total kerf from 25 microns to 18 microns according to the present invention, the diameter after compression is reduced by 0.05 millimeters a significant difference in fully collapsed diameter. Moreover, by reducing the kerf from the conventional 25 microns to 18 microns, a further advantage is obtained—the remaining strut widths are increased due to the fact that less metal is removed. In the present example, reducing total kerf loss from 25 microns to 18 microns, assuming a pre-cut tubing diameter of 2 millimeters and 46 struts, the resulting strut width increases from 112 microns to 119 microns, resulting in a relative stiffness of $(119/112)^3$, or 120%, because stiffness is proportional to the cube of width.

The use of these very narrow kerfs is particularly advantageous to the present invention because of the large number of struts 5 in the configuration—strut counts from 36 to 50, as compared with traditional stents customary strut count, typically in the range of 24 to 32.

Cell Opening Size

The maximum embolus size that can pass through the wall of an expanded stent is determined by the size of the openings between the straight portions 6 and bending segments 7. More precisely, the maximum embolus size is described by the largest circle that can be inscribed within the openings of a particular stent in its open configuration. It is, therefore, desirable to minimize the maximum embolus size to prevent adverse results of embolization in patients.

Referring to FIG. 6 of U.S. Pat. No. 6,129,755 to Mathis et al. (which is hereby incorporated by reference in its entirety), it can be seen that the maximum size embolus that can be passed through the openings between struts has a diameter described by the largest circle that can be inscribed within the space between two adjacent struts and the vertex of a strut pair on the adjacent column of struts. The volume of such an embolus is proportional to the cube of the diameter. So, it can be seen that the volumetric size of the largest embolus that can pass through the stent wall becomes smaller by the third power as the strut geometry is proportionally reduced in size (assuming otherwise similar geometry of the strut openings). From this analysis, it can be appreciated that the clinical effect of emboli can be substantially reduced by using a greater number of shorter struts; hence, clinical safety increases sharply with increases in the M-D Ratio, particularly in regions of the vasculature, such as the carotid arteries, where emboli are poorly tolerated and can have significant deleterious effects upon the patient.

Figure 15:
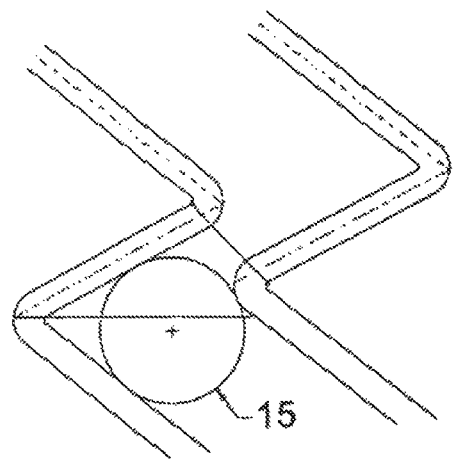
FIG. 15 is a fragmentary, enlarged plan view of a portion of an expanded stent according to the invention illustrating a largest embolism area.
Figure 16:
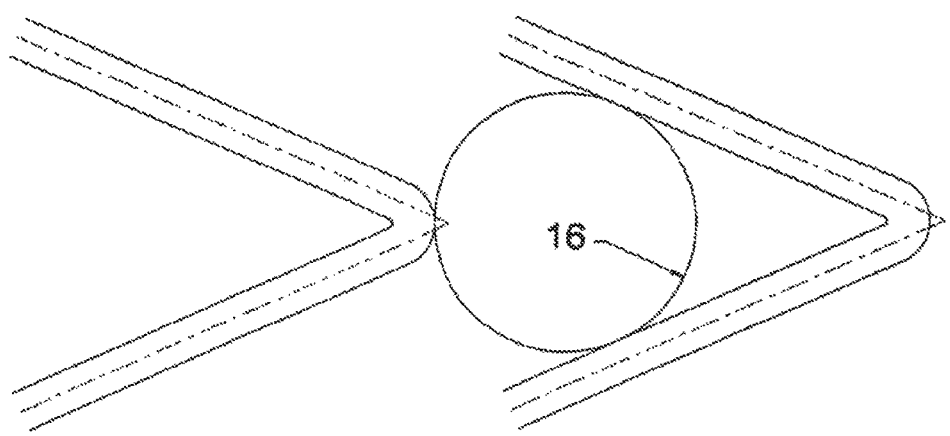
FIG. 16 is a fragmentary, enlarged plan view of a portion of a prior art stent illustrating a largest embolism area.

An expanded helical stent 1 according to the present invention has openings sized to prevent a body (for example an embolus or a substantially spherical body) of greater than approximately 800 microns in diameter from passing therethrough. In a preferred configuration, the expanded helical stent 1 according to the present invention contains 46 struts of 120-micron width and 1000-micron length, for example. Such a configuration results in openings that would allow an inscribed circle 15 of 610 microns. This feature is illustrated in FIG. 15. By comparison, the Cordis 8 mm×50 mm SmartStent allows a much larger inscribed circle. FIG. 16 shows the best-case alignment of the alternate rows of the struts in the SmartStent, allowing an inscribed circle 16 of 1080 microns. The volume of an embolus of 1080 microns versus that of a 610-microns embolus is 5.5 times larger. Thus, it can be seen that the present invention allows a much-increased ability to prevent the passage of clinically significant emboli through its pores.

Another advantage of the present invention in prevention of embolization is realized in the case where the stent 1 is implanted in a bent, or non-straight, configuration. In prior-art stents, bending causes opening of the space or gap between adjacent turns 7 or straight portions 6 of struts on the outside of the bend. Because the present invention teaches the use of very short struts (on the order of between approximately 600 and 1200 microns in length) and, hence, a shorter helical pitch or column-to-column distance, a bending deformation to a stent results in opening of the gaps between several adjacent turns or columns of struts 4. Thus, the distance by which any given gap is widened is reduced in proportion to the number of gaps involved. For example, a stent 1 with struts 5 that are half as long will have twice as many gaps affected by a bend, and the widening of each of these gaps will be reduced by a factor of two.

Smooth Stiffness Gradient from High Bridge Frequency

Because stents 1 made according to the present invention have a relatively high number of features compared with stents made according to the prior art, and because there is a larger number of these features, including the straight portions 6 and the 180-degree loops 5 that provide local flexibility as well as the bridges 8 joining adjacent turns or columns of struts 4 that provide structural integrity to the overall structure, it is possible to fine-tune the flexibility and compression/expansion properties to a much finer extent than in prior-art stents with a substantially smaller number of features. A typical prior-art stent of the same size, for example, the Cordis 8 mm×50 mm SmartStent, has approximately 700 struts. In comparison, for example, an 8-millimeter diameter, 50-millimeter long stent 1 according to the present invention has approximately 1500 struts—more than a 100% increase.

It is possible to adjust the size and width of struts 5 along the length of the stent 1. However, the present invention allows for much more precise use of this conventional construction technique—because the features of the stent 1 are smaller, there are more of them and, thus, the designer has a greater number of features over which to create a gradient of properties such as stiffness, radial outward force, flexural stiffness, surface area (for drug-coating application), and diameter.

In a similar manner, because of the large number of connecting bridges 8, 9 in the configurations taught by the present invention, it is possible to introduce other property gradients along the length of the stent 1. Among the properties affected by bridge frequency and location are flexural stiffness and torsional stiffness. Therefore, it is possible to construct a stent with greater torsional rigidity in the central portion than in the ends, or vice-versa. Similarly, it is possible to provide the stent 1 with more bending flexibility at its ends (and, hence, lower stresses applied to the vessel walls) than in the central segment by placing fewer connecting bridges 8, 9 at the ends of the stent 1 than in the middle. (Of course, the opposite possibility also exists, providing a stent 1 with stiff ends and a more flexible central segment, suitable for use in an area of the body where flexion takes place.)

Short-Pitch Helix

Also, it can be seen that the short length of struts 5 results in a greater helix angle (or, a helical axis more closely approaching perpendicular to the longitudinal axis) for a given circumference of stent because the shorter struts 5 result in a reduced helical pitch. There are several advantages to such an increase in helix angle. First, the unevenness of the distal and proximal ends of the stent is reduced because the step where the end of the helix joins the previous turn is smaller (approximately equal to the stent length). Such a reduced step provides for a stent 1 with a substantially square-cut end (as is typically desired by physicians) in an easier manner.

Second, the increased helix angle results in a stent I that has a reduced tendency to twist as it is expanded. It can be easily imagined that a helical stent with a very low helix angle, similar to a corkscrew, would tend to wobble and twist when released from a confining sheath. As the helix angle is increased toward perpendicular (by reducing the strut length or helical pitch), a helical stent behaves more and more like a non-helical stent constructed of joined cylindrical hoops, resulting in even, non-twisting behavior as it expands when released. Even though some of the resulting properties of a stent with a high helix angle approach those that are advantageous in a non-helical stent (such as a nearly square end and resistance to twisting during expansion), the advantageous properties intrinsic to a helical stent are maintained, such as greater design freedom, lack of distinct rigid and flexible zones along the length of the stent, and more-uniform distribution of applied stresses and strains.

As set forth above, another configuration alternative that becomes practicable with the very short struts 5 of the present invention is the employment of a multiple-helix configuration. As the number of starts is increased in the helix, the ends of the stent 1 begin to become more square-cut in appearance; for example, a triple-helix configuration would have three "notches" at the end where the three loose ends are joined to the adjacent turn. Because it is common to provide radiopaque markers at the ends of stents, these three notches are advantageous locations for three markers, resulting in a symmetrical, even end to the stent 1.

Torsional Compliance and Torsional Fatigue Resistance

The greater number of struts 5 and bridges 8, 9 of the present invention result in the spreading of local forces and deflections brought about in use to a larger number of features, so that these local deformations are spread over a larger number of deforming elements. As a result, each element is proportionately less deformed. It is understandable that a stent with 1500 struts will more readily absorb deformation and in flexion and torsion than a stent with half as many struts, with an attendant reduction in localized loads and deformations to the vessel or other body lumen in which it is placed.

Torsional compliance in a helical stent is determined by the ability of the helical strand of struts 5 to lengthen and shorten. Hence, a longer strand of more numerous struts 5 and their joining bending segments 7 will be better able to absorb lengthening and shortening. The result is, for stents of a given radial compressive strength and outward force, a configuration with a greater number of short struts 5 that will be more easily torsioned than one with a smaller number of longer struts 5. A related result is that, because torsionally induced strains are reduced, any tendency toward fatigue failure caused by torsional motions in-vivo is also reduced.

Flexibility and Bending Fatigue Resistance

In the same way as torsional flexibility and fatigue resistance is improved by increasing the number of flexing elements, the flexural (or bending) flexibility and fatigue resistance are also improved. Bending of a stent causes adjacent turns or columns of struts 4 to be forced either toward each other (on the inside of a bend) or spread apart (on the outside of the bend). Because connecting bridges 8 join adjacent turns or columns 4, the local deformations caused by stent bending are spread over the struts 5 and bending segments 7 (the 180-degree loops that join the ends of struts) between the connecting bridges 8. Thus, the more elements (struts 5 and bending segments 7) that exist between the connecting bridges 8, the greater number of elements there are to absorb the deformations caused by stent bending. Also, in a configuration with shorter struts 5, there is a greater number of turns or columns 4 acted upon by bending the stent 1, so the total number of elements deformed by bending the stent 1 is further increased, resulting in much smaller deformations to each of the elements. As deformations are reduced and shut widths are reduced, the effective strains in the stent material are significantly reduced, resulting in much improved fatigue resistance.

Enhanced Surface Area for Drug Elution

The large number of struts 5 of shorter length in a stent 1 made according to the teachings of the present invention has greater surface area. For example, a stent 1 according to the present teachings will have over twice as much kerf length than an otherwise similar prior art stent with half as many struts around the circumference. In self-expanding stents, kerf area (the area of the cut radial faces of the stent's elements) is the major contributor to total surface area because the area of the inner and outer surfaces is relatively smaller, due to the high aspect ratio (thickness to width) of the struts. Thus, the total surface area of a stent 1 made according to the present teachings is substantially larger than that of a stent made according to prior-art configurations and, thus, it provides a larger surface area on which to apply medicated coatings. This larger surface area allows virtually all tissue within the coverage area of the stent to be in the drug elution areas. In particular, the stent provides tissue coverage so that no element of wall tissue is more than 350 microns to 400 microns away from the nearest strut. Such a configuration assures a short diffusion path from a strut covered with a drug-eluting agent to any portion of the tissue.

What is claimed is:

1. A stent having a reduced state and an expanded state, comprising:
    a series of helical windings including a plurality of struts having a plurality of straight portions connected by a plurality of curved portions,
    a plurality of bridges connecting adjacent windings, wherein each bridge of the plurality of bridges lies in a plane perpendicular to a longitudinal axis of the stent in both the reduced state and the expanded state; and
    a plurality of radiopaque members extending from a terminal helical winding, each of the radiopaque members including an extension portion and an end portion, the extension portion having a first width and the end portion having a second width greater than the first width, the end portion having an extreme end substantially orthogonal to the longitudinal axis of the stent in both the reduced state and the expanded state, wherein the extension portion is adjacent to the terminal helical winding.

2. The stent of claim 1, wherein the end portion of each of the radiopaque members together define a circumferential plane substantially orthogonal to the longitudinal axis of the stent.

3. The stent of claim 1, wherein the extension portion of a first radiopaque member has a length different from the extension portion of a second adjacent radiopaque member.

4. The stent of claim 3, wherein the extension portion of each radiopaque member has a length different from an adjacent radiopaque member.

5. The stent of claim 1, wherein the extreme end of the end portion is circumferentially flat.

6. The stent of claim 1 wherein a helical direction of the windings is opposite of an advancing direction of the bridges.

7. A stent having a reduced state and an expanded state, comprising:
    a series of helical windings, the helical windings including a plurality of struts having a plurality of s-shaped portions or straight portions connected by a plurality of curved portions, the s-shaped portions or straight portions are substantially aligned with a longitudinal axis of the stent in the reduced state;
    a plurality of bridges connecting adjacent windings, wherein each bridge of the plurality of bridges lies parallel to a plane orthogonal to the longitudinal axis of the stent in both the reduced state and the expanded state.

8. The stent of claim 7, wherein the stent further comprises a plurality of radiopaque members extending from a terminal helical winding, each of the radiopaque members including an extension portion and an end portion.

9. The stent of claim 8, wherein the s-shaped portions or the straight portions of at least some of the struts are not aligned with the longitudinal axis in the expanded state.

10. The stent of claim 9, wherein at least some of the struts are v-shaped in the expanded state.

11. The stent of claim 10, wherein the extension portion is adjacent to the helical winding.

12. The stent of claim 11, wherein the series of helical windings form a single helix.

13. The stent of claim 12, wherein one or more of the plurality of struts are s-shaped struts.

14. The stent of claim 13, further comprising sacrificial bridges between adjacent windings.

15. The stent of claim 14, wherein the end portion comprises a radiopaque element.

16. The stent of claim 15, wherein a helical direction of the windings is opposite of an advancing direction of the bridges.

\* \* \* \* \*